(12) United States Patent
Penner et al.

(10) Patent No.: US 8,828,674 B2
(45) Date of Patent: Sep. 9, 2014

(54) FUNCTIONAL IDENTIFICATION OF PROTEINS UNDERLYING ICRAC ACTIVITY IN A CELL

(75) Inventors: Reinhold Penner, Honolulu, HI (US); Andrea Fleig, Honolulu, HI (US)

(73) Assignee: The Queen's Medical Center, Honolulu, HI (US)

( * ) Notice: Subject to any disclaimer, the term of this patent is extended or adjusted under 35 U.S.C. 154(b) by 317 days.

(21) Appl. No.: 12/053,318

(22) Filed: Mar. 21, 2008

(65) Prior Publication Data

US 2009/0053753 A1 Feb. 26, 2009

Related U.S. Application Data

(60) Provisional application No. 60/896,572, filed on Mar. 23, 2007.

(51) Int. Cl.
*G01N 33/567* (2006.01)

(52) U.S. Cl.
USPC .......................................................... 435/7.21

(58) Field of Classification Search
USPC .......................................................... 435/7.21
See application file for complete search history.

(56) References Cited

FOREIGN PATENT DOCUMENTS

WO    WO 2004/078995    9/2004

OTHER PUBLICATIONS

Mercer et al. "Large store-operated calcium selective currents due to co-expression of Orai1 or Orai2 with the intracellylar calcium sensor, Stim1", JBC, 2006, 281(34):24979-24990.*
Prakriya et al. "Potentiation and inhibition of Ca2+ release-activated Ca2+ channels by 2-aminoethyldiphenyl borate (2-APB) occurs independently of IP3 receptors", J of Physiology, 2001, 536.1:3-19.*
Peinelt, Christine et al., "Amplification of CRAC Current by STIM1 and CRACM1 (Orai1)," Nature Cell Biology, v. 8, n. 7, p. 771, Jul. 2006.
Prakriya, Murali et al., "Potentiation and Inhibition of Ca2+ Release-Activated Ca2+ Channels by 2-Aminoethyldiphenyl Borate (2-APB) Occurs Independently of IP3 Receptors," J. of Physiology, v. 536, n. 1 p. 3-19, Oct. 2001.
Putney et al., "Recent Breakthroughs in the Molecular Mechanism of Capacitative Calcium Entry (with thoughts on how we got here)," Cell Calcium (Edinburgh), Churchill Livingstone Medical Journals, Edinburgh, GB v. 42, No. 2, Jul. 10, 2007.
Vig, M., "CRACM1 is a Plasma Membrane Protein Essential for Store-Operated $Ca^{2+}$ Entry," Science, v. 312, n. 5777, p. 1220-1223, May 2006.
Yeromin A.V. et al., "Molecular Identification of the CRAC Channel by Altered Ion Selectivity in a Mutant of Orai," Nature, v. 443, n. 7108, p. 226-229, Sep. 2006.
Hermosura, M.C., et al. "Dissociation of the Store-Operated Calcium $I_{CRAC}$ and the Mg-Nucleotide-Regulated metal Ion Current MagNum," J. of Phys., v. 539, No. 2, p. 445-458, 2002.

* cited by examiner

*Primary Examiner* — Bin Shen
(74) *Attorney, Agent, or Firm* — Morgan, Lewis & Bockius LLP

(57) ABSTRACT

The invention provides methods and compositions for determining the identity of CRACM homologs underlying Icrac activity in cells.

5 Claims, 7 Drawing Sheets

FUNCTIONAL IDENTIFICATION OF PROTEINS UNDERLYING ICRAC ACTIVITY IN A CELL

CROSS REFERENCE TO RELATED APPLICATIONS

The present application claims the benefit of the filing date of U.S. Provisional Patent Application No. 60/896,572, filed Mar. 23, 2007, which is hereby incorporated by reference in its entirety for all purposes.

STATEMENT REGARDING FEDERALLY SPONSORED RESEARCH OR DEVELOPMENT

This invention was made with government support from NIH grant R01-AI050200. The government has certain rights in the invention.

FIELD OF THE INVENTION

The invention relates generally to CRACM homologs and Icrac activity in cells. In particular, the invention provides methods and compositions for determining the identity of CRACM homologs contributing to Icrac activity in cells.

BACKGROUND OF THE INVENTION

In many cell types, store-operated $Ca^{2+}$ entry represents the primary, if not sole, mechanism underlying long-lasting elevations in intracellular $Ca^{2+}$ that follow $IP_3$-mediated release of $Ca^{2+}$ from intracellular stores. Previous investigations have identified STIM1 as the sensor for ER luminal $Ca^{2+}$ concentration and CRACM1 (or Orai1) as the Calcium Release-Activated Calcium (CRAC) channels in the plasma membrane. Upon $Ca^{2+}$ depletion of stores, STIM1 translocates into vesicular structures (puncta) underneath the plasma membrane, where it may bind to and activate multimeric assemblies of CRACM1. When overexpressed jointly, but not individually, STIM1 and CRACM1 reconstitute large CRAC currents. There are three mammalian homologous CRAC channel proteins: CRACM1, CRACM2, and CRACM3. CRACM2 has been shown to enhance store-operated $Ca^{2+}$ entry and produce large CRAC currents when co-expressed with STIM1. Although the same study found that CRACM3 does not enhance store-operated $Ca^{2+}$ entry and no currents have been observed, the protein apparently restored store-operated $Ca^{2+}$ entry to normal levels when CRACM1 was knocked down by siRNA.

Store-operated calcium entry is a ubiquitous element of cell function, and CRAC channels are vital to a wide variety of cellular processes. CRAC channel homologs exhibit distinct electrophysiological and pharmacological properties, and thus a need exists for methods and assays for determining the identity of the CRAC channels contributing to Icrac activity in different cells.

SUMMARY OF THE INVENTION

Accordingly, the present invention provides assays, compositions and methods for determining the contribution of different CRACM channels to Icrac activity in a cell.

In one aspect, the invention provides an assay for determining the contribution of CRACM1 to Icrac activity in a cell. The assay includes measurements of inactivation kinetics, activation kinetics and calcium entry of Icrac activity of said cell. In an embodiment of the invention, a calcium dependent inhibition of the slow inactivation phase of the Icrac inactivation kinetics indicates a contribution of CRACM1 to Icrac activity of said cell.

In another aspect, the invention provides an assay for determining the contribution of CRACM2 to Icrac activity in a cell. The assay includes measurements of inactivation kinetics, activation kinetics and calcium entry of Icrac activity of said cell. In an embodiment of the invention, a calcium dependent inhibition of the slow inactivation phase of the Icrac inactivation kinetics indicates a contribution of CRACM2 to Icrac activity of said cell.

In yet another aspect, the invention provides an assay for determining the contribution of CRACM3 to Icrac activity in a cell. The assay includes measurements of inactivation kinetics, activation kinetics and calcium entry of Icrac activity of said cell. In an embodiment of the invention, a calcium dependent inhibition of the slow inactivation phase of the Icrac inactivation kinetics indicates a contribution of CRACM3 to Icrac activity of said cell.

In one aspect, the invention provides an assay for determining the contribution of CRACM1, CRACM2, and CRACM3 to Icrac activity of a cell comprising measuring ion selectivity of said Icrac activity.

In another aspect, the invention provides an assay for determining the contribution of CRACM1, CRACM2, and CRACM3 to Icrac activity of a cell comprising measuring Icrac activity in the presence of 2-APB.

In a preferred aspect, the contribution of CRACM1, CRACM2, and CRACM3 to Icrac activity in a cell is determined using a measure of a combination of functional properties of Icrac activity, as described in Table I.

TABLE I

Distinguishing features of the functional properties of CRACM homologs

|  | Half-maximal activation times induced by $IP_3$ | Slow inactivation: response to hyperpolarizing pulses to −100 mV | Calcium-dependent slow inactivation induced by buffered intracellular calcium | Effect of 2-APB | Fast inactivation: reduction in current in response to hyperpolarizing pulses to −100 mV |
|---|---|---|---|---|---|
| CRACM1 | 35 ± 7 s | Slow inactivation | Dose-dependent inhibition | Potentiated at concentrations ≤5 μM and inhibited at concentrations ≥10 μM; | 20% |

TABLE I-continued

Distinguishing features of the functional properties of CRACM homologs

| | Half-maximal activation times induced by $IP_3$ | Slow inactivation: response to hyperpolarizing pulses to −100 mV | Calcium-dependent slow inactivation induced by buffered intracellular calcium | Effect of 2-APB | Fast inactivation: reduction in current in response to hyperpolarizing pulses to −100 mV |
|---|---|---|---|---|---|
| CRACM2 | 21 ± 3 s | No slow inactivation | No calcium dependence | complete inhibition in 50 µM 50% inhibition in 50 µM | 50% |
| CRACM3 | 63 ± 7 s | No slow inactivation | No calcium dependence | Potentiated at all measured concentrations in a store-independent manner | 80% |

(indicated by "3"). The bar indicates application of divalent-free external solution. (G) Average normalized CRAC currents ($I/I_{120s}$) at −80 mV induced by $IP_3$ (20 μM) in stable STIM1-expressing HEK293 cells transiently overexpressing CRACM1 (indicated by "1"), CRACM2 (indicated by "2"), or CRACM3 (indicated by "3"). The bar indicates application of external solution containing 50 μM 2-APB.

Figure 5:
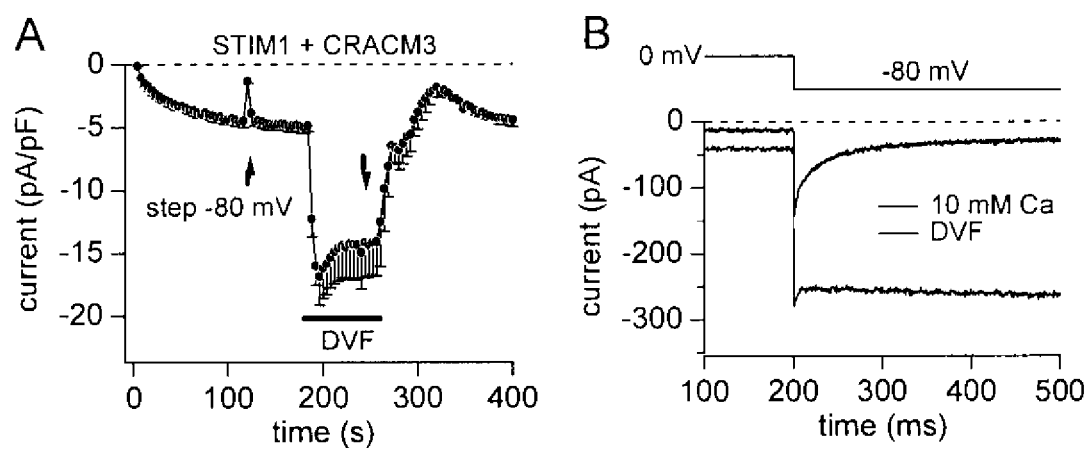

FIG. 5: (A) Average CRAC current densities at −80 mV induced by $IP_3$ (20 μM) with 10 mM EGTA in stable STIM1-expressing HEK293 cells transiently overexpressing CRACM3 (n=3). CRAC currents were monitored continuously by voltage ramps spanning −100 mV to +100 mV over 50 ms delivered at a rate 0.5 Hz. After CRAC currents were fully activated (120 s), a rectangular voltage pulses of 2 s duration was delivered to −80 mV (see panel B). Then the cell was exposed to divalent-free extracellular solution and another voltage pulse was applied. (B) Average CRAC currents evoked by step pulses (2 s duration) to −80 mV in the presence of 10 mM $Ca^{2+}$ (black) and in DVF solution (n=3, same cells as in panel A). Note the loss of inactivation in DVF solution.

Figure 6:
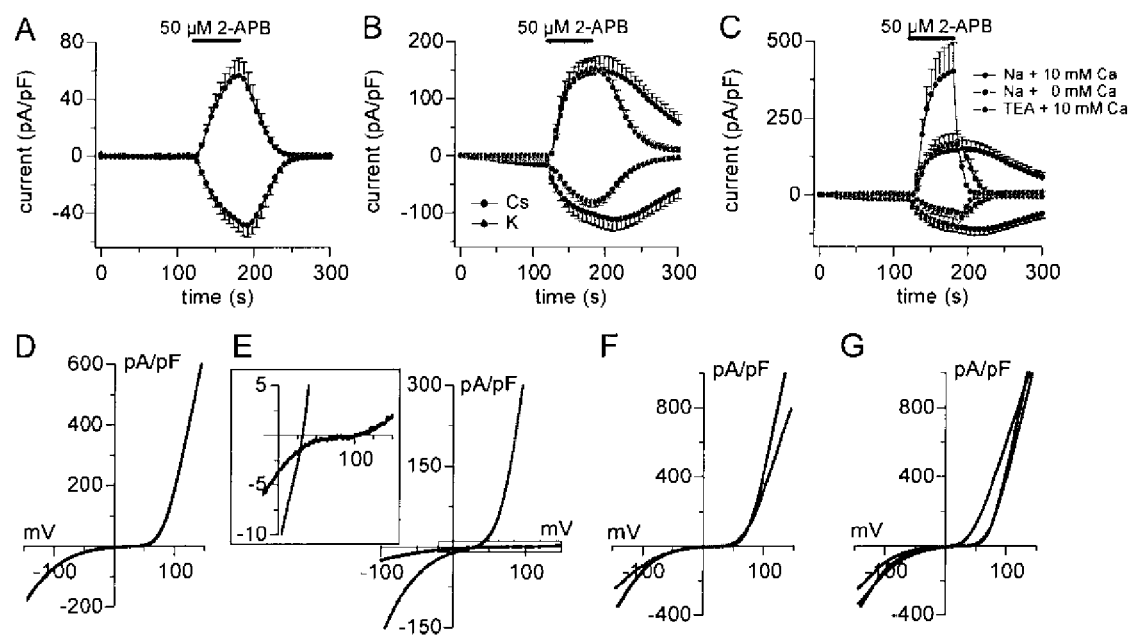

FIG. 6: Store- and STIM-independent activation of CRACM3. (A) Normalized average time course of CRAC currents measured in HEK293 cells overexpressing CRACM3 alone (without STIM1). Currents of individual cells were measured at −80 mV and +80 mV, normalized by cell capacitance, averaged and plotted versus time (n=5± S.E.M.). Internal solution contained 150 nM calcium. The bar indicates application of external solution containing 50 μM 2-APB. (B) Average normalized CRAC currents at −80 mV and +80 mV in STIM1 cells transiently overexpressing CRACM3. Internal solution contained 20 μM $IP_3$. The bar indicates application of external solution containing 50 μM 2-APB in 10 mM Ca Sodium Ringer and internal CsGlu (black, n =9), or internal KGlu (red, n=5). (C) Average normalized CRAC currents at −80 mV and +80 mV in STIM1 cells transiently overexpressing CRACM3. Internal solution contained 20 μM $IP_3$. The bar indicates application of external solution containing 50 μM 2-APB in 10 mM Ca Sodium Ringer (black, n=9, same data as in B), 0 Ca Sodium Ringer (blue, n=5) and 10 mM Ca TEA Ringer (red, n=5). (D) Example IV-curve for the data set shown in panel A at the end of 2-APB application (180 s). (E) Average example IV curves for Cs-data set shown in panel B (n=4). The black trace indicates CRAC currents measured before application of 2-APB (120 s), the red trace at the end of application (180 s). The maanified and boxed inset exemplifies the change in reversal potential due to application of 2-APB (100 mV to 31 mV, respectively). (F) Average example IV curves for Cs and K data set shown in panel B. The black trace indicates CRAC currents measured with internal CsGlu (180 s), the red trace is for internal KGlu. (G) Average example IV curves for data sets shown in panel C at 180 s. The black trace indicates CRAC currents measured in 10Ca/Na Ringer, the red trace is 10Ca/TEA Ringer, and the blue trace is 0Ca/Na Ringer.

Figure 7:
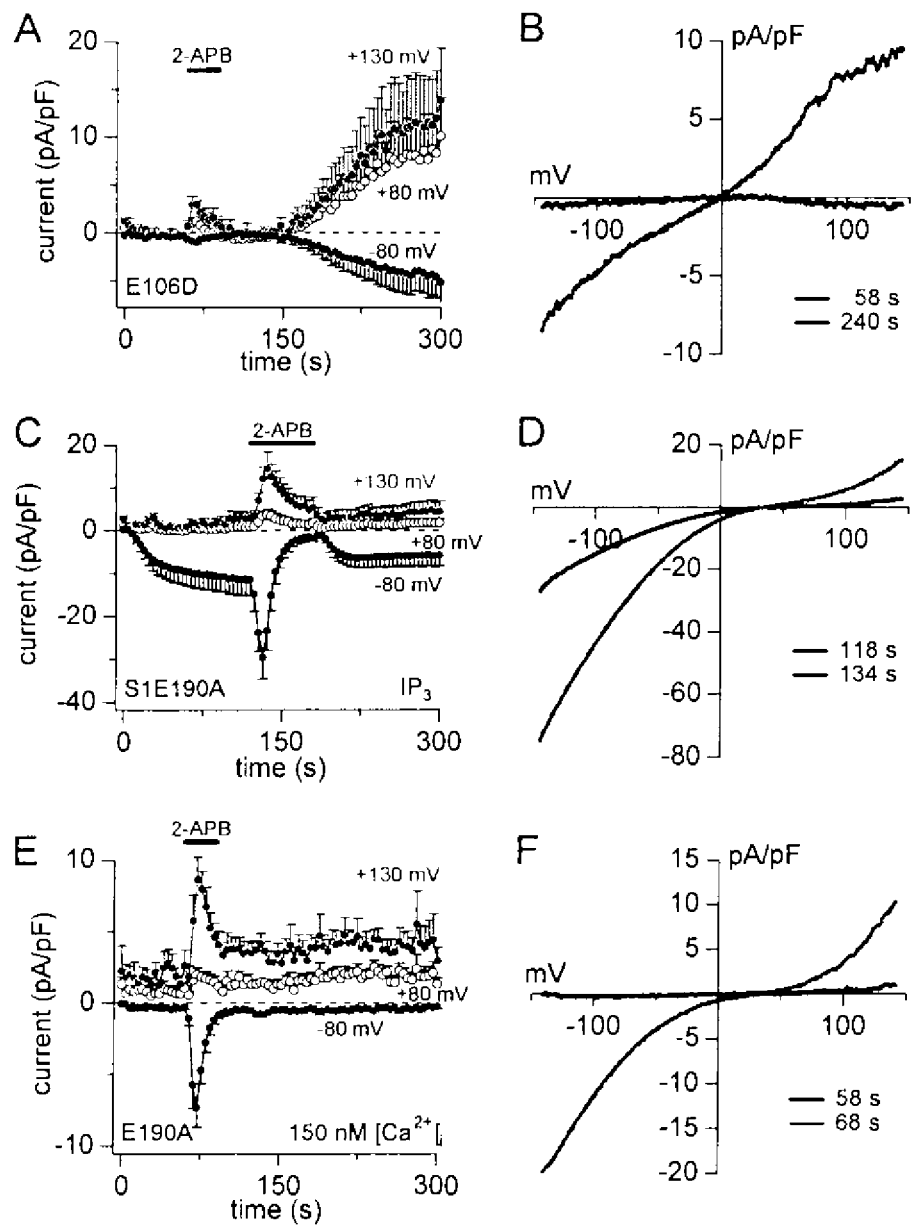

FIG. 7: 2-APB induced current via CRACM1 pore mutants. (A) Average normalized CRAC currents at −80 mV (black), +80 mV (open symbols) and +130 mV (red) in HEK293 wt cells transiently overexpressing CRACM1-E106D. Internal solution was buffered to 150 nM $Ca^{2+}$. The bar indicates application of external solution containing 50 μM 2-APB (n=5). (B) Example I/V-curves for the data set shown in panel A prior to 2-APB application and during CRAC reactivation. (C) Average normalized CRAC currents at −80 mV (black), +80 mV (open symbols) and +130 mV (red) in HEK293 stably expressing STIM1 and transiently overexpressing CRACM1-E190A. Internal solution contained 20 μM $IP_3$. The bar indicates application of external solution containing 50 μM 2-APB (n=9). (D) Example I/V-curves for the data set shown in panel C prior to 2-APB application and at the peak of CRAC current facilitation. (E) Average normalized CRAC currents at −80 mV (black), +80 mV (open symbols) and +130 mV (red) in HEK293 wt cells transiently overexpressing CRACM1-E190A. Internal solution was buffered to 150 nM $Ca^{2+}$. The bar indicates application of external solution containing 50 μM 2-APB (n=8). (F) Example I/V-curves for the data set shown in panel A prior to 2-APB application and at the peak of CRAC current facilitation.

DETAILED DESCRIPTION OF THE INVENTION

Abbreviations

"2-APB" refers to 2-aminoethoxydiphenyl borate.
"$IP_3$" refers to inositol 1,4,5-triphosphate.
"STIM1" refers to Stromal Interaction Molecule 1. Similarly, "STIM2" refers to Stromal Interaction Molecule 2.
"CRAC channel" refers to Calcium Release-Activated $Ca^{2+}$ channel.

DEFINITIONS

The singular forms "a," "an," and "the" include plural references, unless the context clearly dictates otherwise. Thus, for example, references to a composition for delivering "a drug" include reference to one, two or more drugs.

The term "Icrac activity" refers to Calcium Release-Activated Current activity, and can be measured using methods known in the art, including electrophysiology and calcium imaging. Icrac activity may result from the activity of one or more CRAC channel homologs in a cell.

The term "to affect" CRACM homolog activity is used herein to generally refer to any changes to gating, permeability, selectivity and/or expression of the homolog.

INTRODUCTION

CRAC channel proteins are a ubiquitous feature of all cell types, and the ability to identify the CRAC channel homologs underlying Icrac activity in different cells would provide a diagnostic tool for the study of intracellular calcium regulation. Thus, the present invention provides assays and methods for the functional identification of the CRACM homologs underlying Icrac activity in cells.

CRACM channels can be activated by rapid $Ca^{2+}$ store depletion, for example by application of $IP_3$, as well as by passive store depletion, for example by application of a chelator such as BAPTA or a sarc/endoplasmic reticulum calcium ATPase (SERCA) inhibitor such as thapsigargin. The kinetics of activation and inactivation, as well as modulation of calcium entry by these channel homologs can be monitored and measured using techniques known in the art, such as electrophysiology and calcium imaging.

Activation and Inactivation Kinetics of CRACM Homologs

CRAC currents activated in response to rapid calcium store depletion, for example by application of IP3, typically show inwardly rectifying current-voltage relationships. Measurements of the kinetics of activation of these currents can be used in accordance with the present invention to distinguish the contribution of different CRACM homologs to Icrac activity.

When heterologously expressed in HEK293 cells, the average current amplitudes of CRACM2 and CRACM3 at −80 mV are about 3-fold smaller than the corresponding amplitude of CRACM1, but still ~20-fold higher than native CRAC currents in HEK293 cells. The activation kinetics of the CRACM homologs show distinct differences, with half-maximal activation times (±s.e.m) of CRACM1=35±7s (n=12), CRACM2=21±3s (n=8), and CRACM3=63±7s (n=9) (see also FIG. 3E). Thus, in accordance with the present invention, a measurement of the activation kinetics of Icrac activity in a cell can be used to determine the contribution of one or more CRACM homologs.

CRAC currents generally display two phases of inactivation kinetics, a "slow inactivation" phase which occurs over tens of seconds and a "fast inactivation" phase which occurs in the milliseconds range. Such kinetics can be dependent on the level of intracellular calcium. For example, when hyperpolarizing pulses are applied to fully activated CRAC channels, a fast drop in current amplitude is seen with some homologs, such as CRACM2 and CRACM3, which is due to fast inactivation. If a train of hyperpolarizing pulses is applied, the current amplitude of CRACM1, but not that of CRACM2 and CRACM3, decays slowly and recovers slowly over tens of seconds (see FIG. 3) due in part to the slow inactivation process. In the case of CRACM1, the slow inactivation resulting from a series of hyperpolarizing pulses can result in a 50% reduction in CRAC current over a period of approximately 100 seconds. However, a similar experimental protocol in cells expressing CRACM2 or CRACM3 does not elicit the slow inactivation kinetics seen with CRACM1, and only some degree of the fast inactivation phase is apparent. Thus, the present invention provides assays and methods for identifying the contribution of different CRACM homologs to Icrac activity in a cell based on measurements of inactivation kinetics and the calcium dependence of inactivation kinetics.

In one aspect, the invention provides an assay for determining the contribution of CRACM2 to Icrac activity in a cell. The assay includes measurements of inactivation kinetics, activation kinetics and/or calcium entry of Icrac activity of said cell. In an embodiment of the invention, moderate calcium dependent fast inactivation of Icrac kinetics indicates a contribution of CRACM2 to Icrac activity of said cell. As used herein, moderate fast inactivation refers to a fast inactivation which results in a reduction in current amplitude of from about 40% to about 50%. In a preferred embodiment of the invention, a lack of slow calcium induced inactivation and moderate fast inactivation indicates a contribution of CRACM2 to Icrac activity of said cell.

In another aspect, the invention provides an assay for determining the contribution of CRACM3 to Icrac activity in a cell. The assay includes measurements of inactivation kinetics, activation kinetics and calcium entry of Icrac activity of said cell. In an embodiment of the invention, a strong calcium dependent fast inactivation phase of the Icrac inactivation kinetics indicates a contribution of CRACM3 to Icrac activity of said cell. In a further embodiment of the invention, measuring inactivation kinetics comprises measuring the calcium dependence of said inactivation kinetics, and a lack of slow calcium induced inactivation and strong fast inactivation indicates a contribution of CRACM3 to Icrac activity of said cell. As used herein, strong fast inactivation refers to a fast inactivation which results in a reduction in current amplitude of from about 70% to about 80%. In another embodiment the invention provides an assay for determining the contribution of CRACM3 to Icrac activity of a cell in the absence of STIM1.

Ion Selectivity of CRACM Homologs

Mutational analysis has shown that there are several key amino acids in CRACM1 which determine the selectivity of CRAC currents, including glutamate residue 106 in transmembrane segment 1 and glutamate residue 190 in transmembrane segment 3. These residues are thought to form a ring of negatively charged amino acids lining the pore of the channel, and glutamate 106 and 190 are both conserved in all three CRACM homologs.

Another region in the loop between transmembrane segment 1 and transmembrane segment 2 also affects the ion selectivity of CRACM1. This region has three key aspartate residues (D110/D112/D114) that may form a second ring of negative charges to coordinate a second $Ca^{2+}$ ion in the pore. These residues differ among the three homolog, with CRACM2 having E110/Q112/Q114 and CRACM3 having E110/D112/E114. These differences may underlie the differences in the selectivity profiles of the homologs. While the three homologs exhibit similar calcium selectivity for $Ca^{2+}$ over $Na^+$, when all divalent cations are removed, the three homologs show differences in their permeability to $Na^+$ as the charge carrier. When all cations are removed and in addition 10 mM EDTA is applied to chelate any residual cations, CRAC channels become permeable to $Na^+$, typically generating a twofold increase in inward current in HEK293 cells overexpressing CRACM1. The same experimental protocol produces slightly larger CRACM2 currents and CRACM3 generates a significantly larger monovalent current.

In one aspect, the invention provides an assay for determining the contribution of CRACM1, CRACM2, and CRACM3 to Icrac activity of a cell which includes measuring ion selectivity of said Icrac activity. In a preferred embodiment, the level of Icrac activity when $Na^+$ is the charge carrier indicates a level of contribution of CRACM1, CRACM2, CRACM3, or some combination thereof to said Icrac activity.

Heteromultimers of CRACM Homologs

Figure 1:
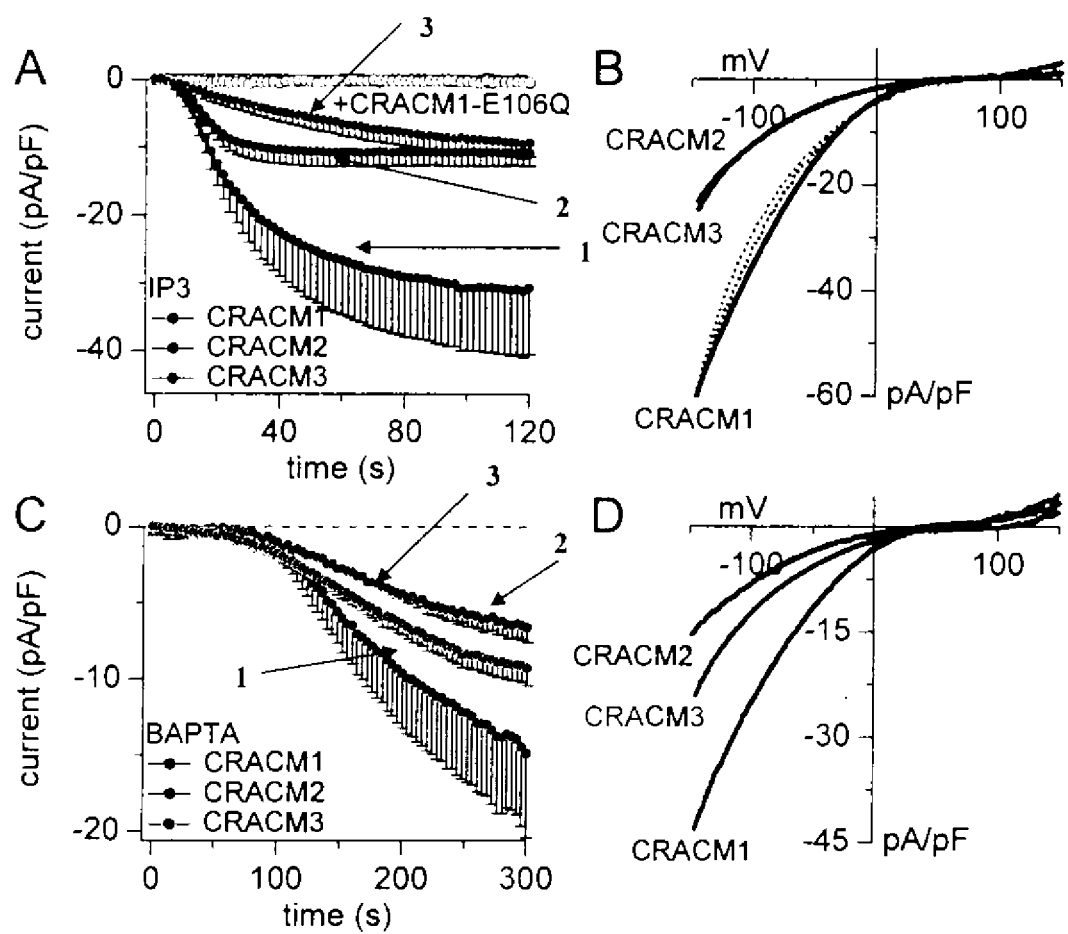
FIG. 1: (A) Average CRAC current densities at −80 mV induced by IP, (20 µM) in stable STIM1-expressing HEK293 cells transiently overexpressing CRACM1 (indicated with "1"), CRACM2 (indicated with "2"), and CRACM3 (indicated with "3"). Open symbols represent cells that were co-transfected with the wildtype constructs of the three homologs plus the dominant negative E106Q mutant of CRACM1 (CRACM1-E106Q+CRACM1 n=6, +CRACM2 n=6, +CRACM3 n=7). $[Ca^{2+}]_i$ was clamped to near zero with 20 mM BAPTA. (B) Average current-voltage (I/V) relationships of CRAC currents extracted from representative HEK293 cells shown in panel A obtained at 120 s. Data represent leak-subtracted current densities (pA/pF) evoked by 50 ms voltage ramps from −150 to +150 mV corresponding to CRACM1, CRACM2, and CRACM3. The dotted traces correspond to the CRACM2 and CRACM3 I/Vs, but scaled to match the CRACM1 amplitude at −140 mV. (C) Average CRAC current densities following passive store depletion using 20 mM BAPTA and omitting IP, in cells expressing CRACM1 (indicated with "1"), CRACM2 (indicated with "2"), and CRACM3 (indicated with "3"). Currents were analyzed as in panel A. (D) Average I/V traces extracted from representative HEK293 cells shown in panel C at 300 s in to the experiment. Traces correspond to CRACM1, CRACM2, and CRACM3.

CRACM1 has been shown to form multimeric channel complexes. A non-conducting pore mutation of CRACM1 (E106Q) confers a dominant negative phenotype on native CRAC channels and can be used to establish whether other CRACM homologs can form multimers with CRACM1. Combined over-expression of CRACM1-E106Q in equal amounts with wildtype CRACM2 and CRACM3 essentially abolished CRAC currents carried by either of the CRACM homologs, suggesting that the channel homologs can form heteromultimers. (see FIG. 1). The kinetics and calcium entry activity of these heteromultimers can be used in accordance with the present invention to identify the contribution of different CRACM homologs and CRACM heteromultimers to Icrac activity in a cell. In one embodiment, the assays of the invention include a comparison of the activity of CRACM heteromultimers heterologously expressed in a cell line against Icrac activity in a native cell to determine the contribution of different CRACM homologs underlying the Icrac activity in the native cell. In a further embodiment, this assay involves comparison of ion selectivity, gating, pharmacology, and permeability between the heterologously expressed CRACM homologs and heteromultimers and the Icrac activity in the native cell.

Pharmacology of CRACM Homologs

One way to identify and analyze the contribution of different CRACM homologs to Icrac activity in a cell is through the use of pharmacology. In one aspect of the invention, a pharmacological agent that affects different homologs in different ways can be used to determine the effect of one or more homologs on the Icrac activity in the cell.

In one aspect, 2-aminoethoxydiphenyl borate (2-APB) is used as a tool to identify and analyze the contribution of different CRACM homologs to Icrac activity in a cell. 2-APB is a compound that has facilitatory effects on CRACM1 currents at low doses (≤5 µM), but inhibits them at high doses (≥10 µM), with complete inhibition of CRACM1 seen at 50 µM 2-APB. However, CRACM2 is significantly less sensitive to 2-APB-mediated inhibition, and CRACM3 is surprisingly greatly potentiated by 2-APB over the same range of 2-APB concentrations.

In one aspect, the invention provides an assay for determining the contribution of CRACM1, CRACM2, and CRACM3 to Icrac activity of a cell comprising measuring Icrac activity in the presence of 2-APB. Potentiation of Icrac current in the presence of 2-APB indicates a contribution of CRACM3 to said Icrac activity. In an embodiment of the invention, potentiation of Icrac current at concentrations less than or equal to 5 µM 2-APB and inhibition of Icrac current in the presence of greater than or equal to 10 µM 2-APB indicates a contribution of CRACM1 to said Icrac activity.

In the absence of STIM1 overexpression, CRAC currents are typically less than 1 pA/pF even when stores are depleted. However, 50 µM 2-APB can activate large CRAC currents by activating CRACM3 channels directly. Similar responses can be evoked in the absence of $IP_3$ and when buffering intracellular $Ca^{2+}$ to 150 nM to avoid store depletion (n=6, data not shown). Hence, the 2-APB-induced currents are store- and STIM-independent. This mechanism can be exploited to activate CRACM3 without STIM overexpression and to measure currents or $Ca^{2+}$ signals for drug screening purposes.

In a further aspect, 2-APB can be used to assess the activity of Icrac and its component CRACM homologs by altering the selectivity of CRAC channels. In one embodiment, the application of 2-APB alters the selectivity of CRACM3 (See FIG. 6). In one aspect of the invention, altering the selectivity of CRACM homologs using 2-APB allows the use of Na+ indicators or with voltage-sensitive dyes to further identify the contribution of different CRACM homologs to Icrac activity in a cell. For example, 2-APB-evoked CRACM3 current exhibits strong rectification at negative and positive membrane voltages, with a reversal potential of +30 mV (see FIG. 6D). Normally, CRAC currents are highly $Ca^{2+}$ selective and poorly permeable to $K^+$ or $Cs^+$, resulting in positive reversal potentials. However, the outward currents observed with CRACM3 when cells are exposed to 2-APB shows a significant increase in monovalent $Cs^+$ permeation and a large shift in reversal potential.

In a further aspect, the invention provides assays for CRACM homolog activity in response to analogs of 2-APB. Such analogs are known in the art, for example analogs with variations in the substituents to the oxazaborolidine ring (methyl, dimethyl, tert-butyl, phenyl, methyl phenyl, and pyridyl), and analogs in which the size of the oxazaborolidine rings are increased to seven- and nine-membered rings. Other analogs 2-APB which may be used in accordance with the invention include structural analogs such as phenolphthalein and phenolphthalein derivatives.

CRAC Channels and Disease

A number of diseases, including but not limited to immunodeficiency disease, neurological disease, and cardiovascular disease, are associated with mutations in CRAC channels. For example, a genetic defect has been described in which mutations in a key component of CRAC channels result in T lymphocyte malfunction and Severe Combined Immunodeficiency Disease (SCID). (Partiseti et al., J Biol. Chem. (1994) 269: 32327-35; Feske et al., Nature (2006) 441:179-85). A powerful tool in the study, diagnosis and treatment of these diseases and other CRAC related diseases is the ability to identify (1) the CRAC channel homologs which underlie the Icrac activity in these disease states and (2) agents that modulate such CRAC channels.

In accordance with the present invention, an assay is provided which can identify the contribution of CRACM1, CRACM2, and/or CRACM3 to Icrac activity in cells associated with a disease. In a preferred embodiment, the assay comprises measuring Icrac activity, particularly activation kinetics, inactivation kinetics, calcium entry, ion selectivity and permeation. In a further embodiment, the assay comprises measuring the differential pharmacological effects of 2-APB on the homologs.

The present invention may be better understood by reference to the following non-limiting Examples, which are provided as exemplary of the invention. The following examples are presented in order to more fully illustrate preferred embodiments of the invention, but should in no way be construed as limiting the broad scope of the invention.

EXAMPLES

Example I

Heterologous Expression Of CRACM Homologs

To assess the functional properties of CRACM proteins, all three CRACM species were overexpressed in HEK293 cells. CRAC currents were measured in response to rapid Ca2+ store depletion by 20 µM inositol 1,4,5-trisphosphate ($IP_3$) as well as following passive store depletion by perfusing cells with 20 mM BAPTA, which results in a slower store depletion that relies on Ca2+ leaking from stores. Full length human CRACM1 (accession no. $NM_{032790}$) and CRACM1-E106Q were subcloned as described. Full length human CRACM2 (accession no. $NM_{032831}$) and CRACM3 (accession no. $NM_{152288}$) were amplified from cDNAs (purchased from Origene) using high fidelity Pfu Ultra High Fidelity polymerase (Stratagene) and subcloned into pCAGGS-IRES-GFP vector. The ribosome binding site SEQ ID NO: 1: ACC GCC ACC and a HA-tag were introduced in frame immediately 5' to the start codon of CRACM2 and CRACM3 cDNAs, which were subsequently cloned into pCAGGS-IRES-GFP for transient dicistronic expression of CRACM2 and CRACM3 together with the green fluorescent protein (GFP). CRACM proteins were over-expressed in HEK293 cells stably expressing STIM1 using lipofectamine 2000 (Invitrogen) and the GFP expressing cells were selected by fluorescence.

Figure 2:
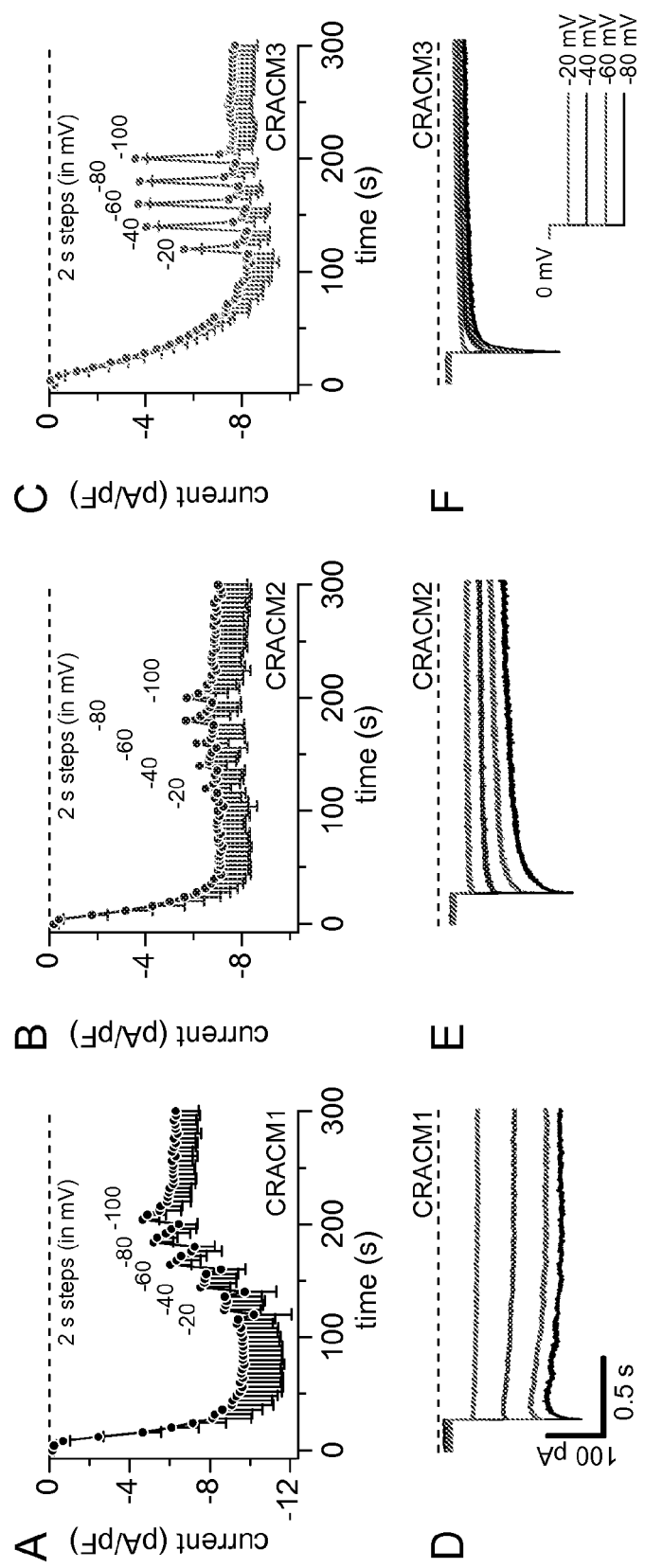
FIG. 2: Average CRAC current densities at −80 mV induced by $IP_3$ (20 µM) with 10 mM EGTA in stable STIM1-expressing HEK293 cells transiently overexpressing (A) CRACM1; (B) CRACM2 and (C) CRACM3. (D). Average CRAC currents evoked by step pulses (2 s duration) to −20 mV, −40 mV, −60 mV, and −80 mV in cells expressing. At the beginning of each pulse, 2.5 ms were blanked out to eliminate residual capacitative artifacts. (E) Average CRAC currents evoked by step pulses from −20 mV to −80 mV in cells expressing CRACM2. (F) Average CRAC currents evoked by step pulses from −20 mV to −80 mV in cells expressing CRACM3.

Patch-clamp experiments were performed in the tight-seal whole-cell configuration at 21-25° C. High-resolution current recordings were acquired using the EPC-9 (HEKA). Voltage ramps of 50 ms duration spanning a range of −150 to +150 mV were delivered from a holding potential of 0 mV at a rate of 0.5 Hz over a period of 100-300 sec. All voltages were corrected for a liquid junction potential of 10 mV. Currents were filtered at 2.9 kHz and digitized at 100 µs intervals. Capacitive currents were determined and corrected before each voltage ramp. Extracting the current amplitude at −80 mV from individual ramp current records assessed the low-resolution temporal development of currents. Where applicable, statistical errors of averaged data are given as means± S.E.M. with n determinations. Standard external solutions were as follows (in mM): 120 NaCl, 2 $MgCl_2$, 10 $CaCl_2$, 10 TEA-Cl, 10 HEPES, 10 glucose, pH 7.2 with NaOH, 300 mOsm. In some experiments, $Na^+$-free solutions were applied, where NaCl was replaced equimolarly by tetraethylammonium-chloride (TEA-Cl). For $Ca^{2+}$-free external solutions $CaCl_2$ was omitted, but $Mg^{2+}$ was retained. The divalent-free external solution (DVF) was based on the standard external solution but in the absence of $CaCl_2$ and $MgCl_2$ and additionally supplemented with 10 mM EDTA. Divalent replacement solutions were based on the standard external solution but with 10 mM $CaCl_2$ replaced by 10 mM $BaCl_2$. In some experiments, 2-aminoethyldiphenyl borate (2-APB) was added to the standard external solution at a final concentration of 50 µM. Standard internal solutions were as follows (in mM): 120 Cs-glutamate, 20 Cs-BAPTA, 3 $MgCl_2$, 10 HEPES, 0.02 $IP_3$, pH 7.2 with CsOH, 300 mOsm. In the experiments of FIG. 2, 10 mM EGTA was used and in FIG. 3, $[Ca^{2+}]_i$ was buffered to defined levels using 20 mM Cs-BAPTA and appropriate concentrations of $CaCl_2$ as calculated with WebMaxC. For passive-depletion experiments, $IP_3$ was omitted from the internal solution. All chemicals were purchased from Sigma-Aldrich Co.

Wild-type HEK293 cells normally exhibit native CRAC currents of 0.5 pA/pF, with typical inwardly rectifying current-voltage (I/V) relationships. The simple over-expression of CRACM2 or CRACM3 in wild-type HEK cells did not have a significant effect on the endogenous CRAC currents, consistent with the additional requirement of STIM1 to produce amplified CRAC currents. Transient over-expression of CRACM2 or CRACM3 in HEK293 cells that stably overexpress STIM1 cells produced large membrane currents in both CRACM2- and CRACM3-expressing cells upon store depletion with $IP_3$ (FIG. 1A) with inwardly rectifying current-voltage (I/V) relationships characteristic of $I_{CRAC}$ (FIG. 1B).

Example II

Activation Kinetics and Voltage Dependent Behavior of CRACM Homologs

When co-expressed with STIM1, the average current amplitudes of CRACM2 and CRACM3 at −80 mV were about 3-fold smaller than the corresponding amplitude of CRACM1, but still ~20-fold higher than native CRAC currents in HEK293 cells. The activation kinetics of the CRACM homologs were distinctly different, with half-maximal activation times (±s.e.m) of CRACM1=35±7s (n=12), CRACM2=21±3 s (n=8), and CRACM3=63±7s (n=9) (see also FIG. 3E). The average I/V relationships of the three channels, when scaled to match at −140 mV (dotted lines in FIG. 1B), exhibit slight differences in rectification, with CRACM3 having the most pronounced curving, which is due to its very pronounced fast $Ca^{2+}$-dependent inactivation (See FIG. 2).

CRACM channel activation by passive store depletion with 20 mM BAPTA in the absence of $IP_3$ was investigated. All three CRACM species produced CRAC-like currents with a characteristic delay that reflects the time needed to passively deplete stores through leak pathways. The I/V relationships (FIG. 1D) confirm that these currents have a shape characteristic of CRAC currents. Taken together, these results demonstrate that all three CRACM homologs, when co-expressed with STIM1, are capable of generating amplified store-operated CRAC currents upon active or passive store depletion.

Example III

CRACM Heteromultimers

Given that all three homologs produced store-operated channels and CRACM1 have been shown to form multimeric channel complexes, a non-conducting pore mutation of CRACM1 (E106Q) that confers a dominant negative phenotype on native CRAC channels was used to assess whether CRACM1 can assemble into heteromeric channel complexes with CRACM2 and/or CRACM3. FIG. 1A illustrates that the combined over-expression of CRACM1-E106Q in equal amounts with wildtype CRACM proteins essentially abolished CRAC currents carried by either of the CRACM homologs, suggesting that the CRACM1 pore mutant indeed confers a dominant negative effect. Average current amplitudes at 100-120 s and −80 mV for the three homologs co-expressed with CRACM1-E106Q were: CRACM1 0.15±0.15 pA/pF (n=6), CRACM2 0.19±0.13 pA/pF (n=6), and CRACM3 0.33±0.28 pA/pF (n=7), all of which are lower than endogenous CRAC currents in STIM1 expressing HEK293 cells (0.69±0.27 pA/pF (n=14)). These results show that CRACM1 is able to form heteromeric channels with both of its homologs.

Example IV

Inactivation Kinetics of CRACM Homologs

Native CRAC currents are regulated by $[Ca^{2+}]_i$ and subject to both fast and slow $Ca^{2+}$-dependent inactivation. Fast inactivation, occurring in the milliseconds range, is believed to result from $Ca^{2+}$ binding to the channel itself, whereas slow inactivation over tens of seconds may result from store refilling and/or regulatory mechanisms through cellular feedback mechanisms on the channel. The differences in the inward rectification of the CRACM homologs seen in FIG. 1B indicate differences in fast inactivation kinetics for the various homologs. FIG. 2 illustrates experiments in which CRAC currents carried by the three homologs were induced by 20 µM $IP_3$ using intracellular solutions that contained 10 mM EGTA. This chelator is slower in chelating $Ca^{2+}$ and therefore less efficient in suppressing fast $Ca^{2+}$-dependent inactivation than BAPTA. If sufficient $Ca^{2+}$ accumulates intracellularly, the buffering capacity of EGTA is overpowered to reveal slow $Ca^{2+}$-dependent processes.

CRAC currents were monitored continuously by voltage ramps spanning −100 mV to +100 mV over 50 ms delivered at a rate 0.5 Hz. After CRAC currents were fully activated, rectangular voltage pulses of 2 s duration and increasing negative voltages were delivered so as to increase $Ca^{2+}$ entry. Panels A-C of FIG. 2 illustrate that each hyperpolarizing pulse caused a fast drop in CRACM1 current amplitude that slowly, but not completely recovered before the next pulse was delivered. The fast drop in current is due to fast inactivation and the recovery is likely the net result of two opposing effects, recovery of channels from fast inactivation and slow inactivation proceeding over tens of seconds (see also FIG. 3). In the case of CRACM1, the slow inactivation resulting from the five hyperpolarizing pulses resulted in about 50% reduction in CRAC current over a period of ~100 seconds. In marked contrast, the same experimental protocol performed in cells expressing CRACM2 or CRACM3 revealed only fast inactivation of currents with no significant slow inactivation (FIG. 2, B and C). CRACM2 appeared fairly resistant to $Ca^{2+}$-induced inactivation in general, with only a small component of fast inactivation, whereas CRACM3 displayed a much larger degree of fast inactivation. In both cases, recovery from fast inactivation was essentially complete within 20 s.

Panels D-F of FIG. 2 illustrate averages of high-resolution CRAC currents produced by the hyperpolarizing pulses in panels A-C, revealing the degree of fast $Ca^{2+}$-dependent inactivation of the three homologs. CRACM3 currents exhibit a striking $Ca^{2+}$-dependent inactivation that at −80 mV is characterized by a predominant exponential decay with a time constant of τ=17 ms and very small slow component $\tau_2$=130 ms. This dramatic inactivation of CRACM3 is primarily due to $Ca^{2+}$. In experiments where a similar protocol as in FIG. 2C was followed by delivering a hyperpolarizing voltage pulse to −80 mV in the presence of 10 mM $Ca^{2+}$ and after switching to DVF solution, a rapidly inactivating current while $Ca^{2+}$ was present and a sustained, non-inactivating current when divalent cations were absent were revealed (see FIG. 5). CRACM2 exhibits moderate fast $Ca^{2+}$-dependent inactivation, decaying with two time constants of $\tau_1$=80 ms and $\tau_2$=900 ms that both contribute in roughly equal amounts to total fast inactivation. CRACM1 exhibits complex behavior that may reflect three $Ca^{2+}$-dependent feedback effects and therefore cannot be readily assessed quantitatively in terms of time constants. The slow inactivation of CRACM1 currents is not obvious in the recordings shown in FIG. 2D, as it occurs over tens of seconds (see FIG. 2A). However, slow inactivation is reflected by the overall reduced current amplitudes obtained by the negative pulses, as they are smaller than predicted from the inwardly rectifying I/V.

Figure 3:
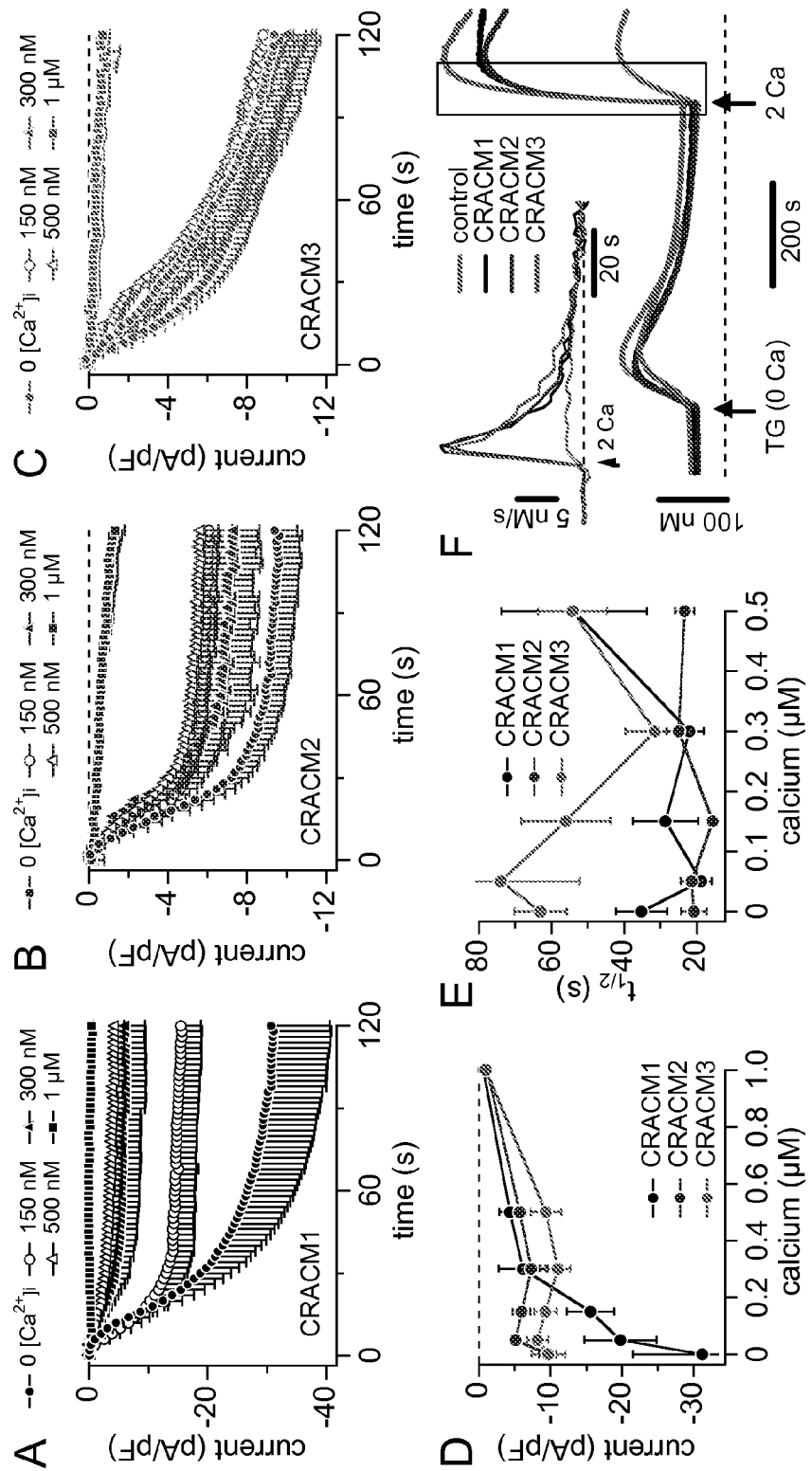
FIG. 3: Average CRAC current densities at −80 mV induced by $IP_3$ (20 µM) in stable STIM1-expressing HEK293 cells transiently overexpressing (A) CRACM1, (B) CRACM2, and (C) CRACM3-expressing cells. (D) Average current densities of CRACM1 (black), CRACM2 (blue), and CRACM3 (red) at −80 mV extracted at 120 s (150 s for CRACM3) from the cells shown in panels A-C and plotted versus $[Ca^{2+}]_i$. (E) Half-maximal activation time of CRACM1 (indicated by "1"), CRACM2 (indicated by "2"), and CRACM3 (indicated by "3") plotted versus $[Ca^{2+}]_i$. Data were derived from the cells shown in panels A-C. (F) Average changes in $[Ca^{2+}]_i$ induced by store depletion in stable STIM1-expressing HEK293 cells transfected with empty vector (green, n=14), or transiently overexpressing CRACM1 (indicated by "1"), CRACM2 (indicated by "2"), or CRACM3 (indicated by "3"). The arrows indicate application of thapsigargin (2 µM) in $Ca^{2+}$-free solution to induce store depletion and readmission of 2 mM $Ca^{2+}$ to probe $Ca^{2+}$ entry. The inset represents rates of $[Ca^{2+}]_i$, obtained by differentiating the trace segment enclosed by the rectangle.

To assess the slow $Ca^{2+}$-dependent inactivation of CRAC currents, cells were perfused with 20 mM BAPTA and appropriate amounts of $CaCl_2$ so that free $[Ca^{2+}]_i$ was clamped to defined levels between 0 and 1 μM. CRAC currents were induced by $IP_3$ and monitored by voltage ramps. The results illustrated in FIG. 3A demonstrate that increasing $[Ca^{2+}]_i$, dose-dependently inhibited CRACM1 currents, but had little or no significant effect on CRACM2 or CRACM3 (FIG. 3, B and C). The absence of significant slow inactivation seen with CRACM2 or CRACM3 is likely of some importance in the physiological context as intermediate $[Ca^{2+}]_i$ levels occurring physiologically (300-500 nM) would tend to maintain activity of CRACM2 and CRACM3 channels, whereas CRACM1 currents would be significantly reduced. Only at 1 μM $[Ca^{2+}]_i$ were the CRACM2 and CRACM3 currents suppressed almost as strongly as those carried by CRACM1.

Example V

Calcium Dependence of CRACM Homolog Kinetics and Modulation of Calcium Entry

The effect of $[Ca^{2+}]_i$ on the kinetics of CRAC current activation were examined by determining the time to half-maximal activation ($t_{1/2}$). This parameter was generally independent of $[Ca^{2+}]_i$ for CRACM2 and CRACM1, which both had similarly fast activation kinetics (FIG. 3E). At low $[Ca^{2+}]_i$ levels, CRACM3 currents activated significantly slower than those of the other homologs, but accelerated at intermediate $[Ca^{2+}]_i$ of 150-300 nM (FIG. 3E). The kinetic differences as well as the degrees of fast and slow $Ca^{2+}$-dependent inactivation between the CRACM homologs can be useful in identifying CRACM species in cells that express them natively.

For $Ca^{2+}$ measurements, fura-2 AM (Molecular Probes, Eugene, Ore., USA) loaded cells (1 μM/60 min/37° C.) were kept in extracellular saline containing (in mM): 140 NaCl, 2.8 KCl, 2 $MgCl_2$, 10 glucose, 10 HEPES-NaOH, pH 7.2. Store depletion was induced by adding 2 μM thapsigargin to the bath and for assessing store-operated $Ca^{2+}$ entry, 2 mM $Ca^{2+}$ was added. Experiments were performed with a Zeiss Axiovert 100 fluorescence microscope equipped with a dual excitation fluorometric imaging system (TILL-Photonics, Gräfelfingen, Germany), using a 40× Plan NeoFluar objective. Data acquisition and computation was controlled by TILLvisION software. Dye-loaded cells were excited by wavelengths of 340 and 380 nm, produced by a monochromator (Polychrome IV). The fluorescence emission of several single cell bodies was simultaneously recorded with a video camera (TILL-Photonics Imago) using an optical 440 nm longpass filter. The signals were sampled at 0.5 Hz and computed into relative ratio units of the fluorescence intensity at the different wavelengths (340/380 nm). Results are given as the approximate $[Ca^{2+}]_i$, calculated from the 340/380 nm fluorescence values, using an in vivo $Ca^{2+}$ calibration performed in patch-clamp experiments with defined $Ca^{2+}$ concentrations combined with fura-2 in the patch pipette.

If slow $Ca^{2+}$-dependent inactivation affects the CRACM1 currents in the manner described above, then it would be expected to at least partially affect the amount of $Ca^{2+}$ entry observed in intact cells, where $[Ca^{2+}]_i$ increases due to CRAC channel activity. Fura-2 signals were monitored in cells overexpressing the various CRACM proteins. The cells were subjected to a standard protocol where store-depletion was induced by thapsigargin in the absence of extracellular $Ca^{2+}$, followed by readmission of 2 mM $Ca^{2+}$ to probe store-operated $Ca^{2+}$ entry (FIG. 3F). In empty vector-transfected cells, $Ca^{2+}$ readmission caused a moderate increase in $[Ca^{2+}]_i$ by store-operated entry through endogenous CRAC channels. Cells overexpressing CRACM homologs produced significantly larger changes in $[Ca^{2+}]_i$ that are even more impressive when analyzing the rate of $Ca^{2+}$ entry by differentiating the fura-2 signals (see inset in FIG. 3F). Although CRACM1 is capable of generating 3-fold larger currents compared to CRACM2 or CRACM3 when $[Ca^{2+}]_i$ is buffered to near zero (see FIG. 1A), all three homologs achieve similar absolute levels in $[Ca^{2+}]_i$ and initial rates of $Ca^{2+}$ entry when assessed by fura-2 in intact cells. The reason for this is presumably due to the more pronounced slow $Ca^{2+}$-dependent inactivation, which limits the rate of $Ca^{2+}$ entry for CRACM1 and prevents a larger increase in $[Ca^{2+}]_i$. Thus, the $[Ca^{2+}]_i$ signals obtained in intact cells, where global $[Ca^{2+}]_i$ increases into the range of 300-500 nM, are comparable to the amplitudes of CRAC currents observed when clamping global $[Ca^{2+}]_i$ to defined levels of that range (see FIG. 3D).

Example V

Ion Selectivity of CRACM Homologs

Previous work on CRACM1 has identified critical residues in three regions of the protein that affect selectivity of the channel. Glutamate residue 106 in transmembrane (TM) segment 1 and glutamate residue 190 in TM 3 are thought to form a ring of negatively charged amino acids lining the pore of the channel. Both of these residues are conserved identically in all three CRACM homologs and are therefore unlikely to account for differential selectivity among the three homologs. However, a third region located in the loop between TM 1 and TM 2 also affects selectivity of CRACM1. This region has three key aspartate residues (D110/D112/D114) that may form a second ring of negative charges that coordinates a second $Ca^{2+}$ ion to the CRACM1 pore and those residues differ in the three homologs (CRACM2 has E110/Q112/Q114 and CRACM3 has E110/D112/E114).

Figure 4:
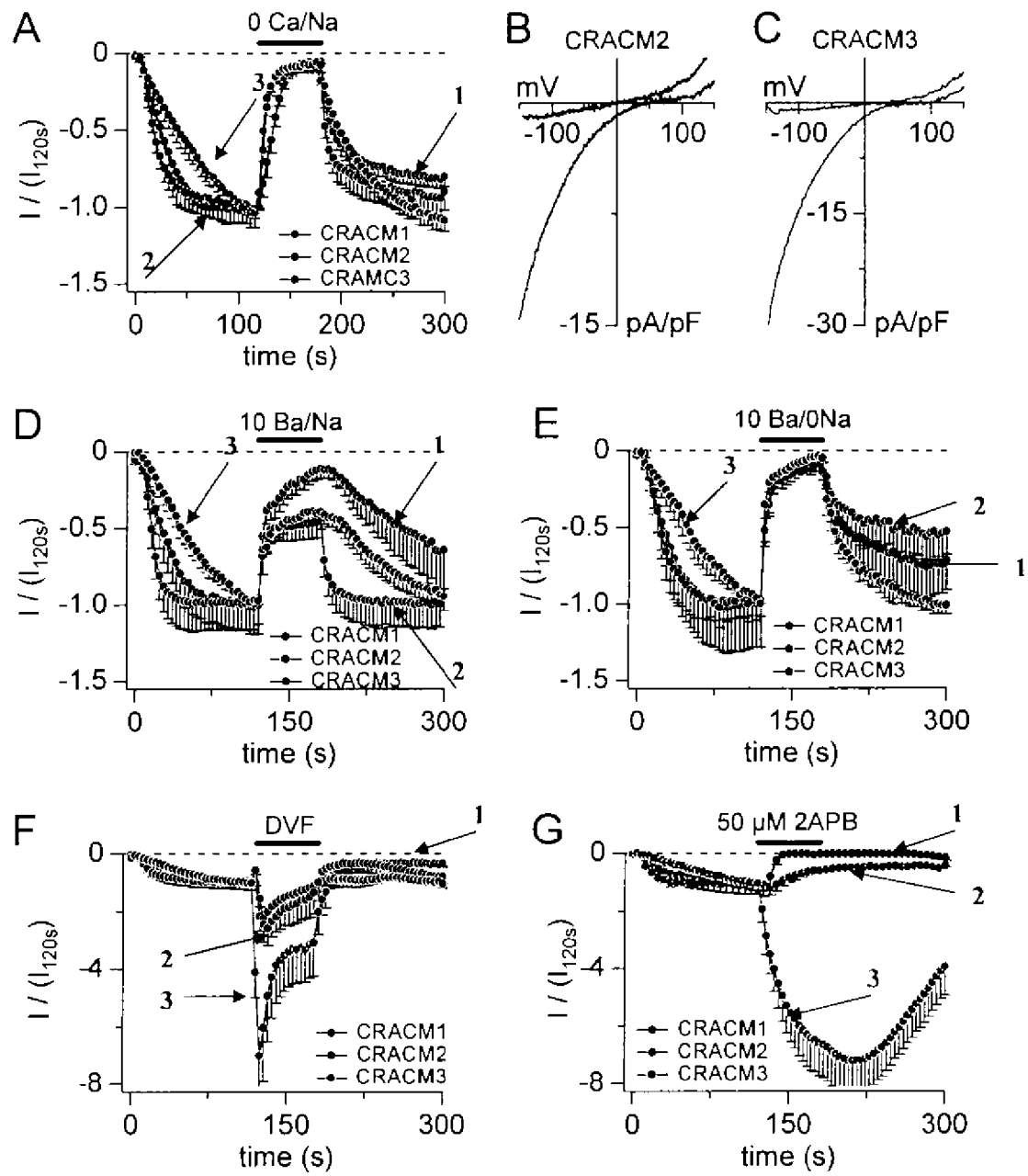
FIG. 4: (A) Average normalized CRAC currents at −80 mV induced by $IP_3$ (20 µM) in stable STIM1-expressing HEK293 cells transiently overexpressing CRACM1 (indicated by "1") CRACM2 (indicated by "2"), or CRACM3 (indicated by "3"). Currents of individual cells were normalized to the current before solution change at 120 s ($I/I_{120s}$). $[Ca^{2+}]_i$ was clamped to near zero with 20 mM BAPTA. The bar indicates application of nominally $Ca^{2+}$-free external solution. (B) Average I/V relationships of CRACM2 currents extracted from representative cells shown in panel A obtained at 120 s and 180 s (n=7). Data represent leak-subtracted current densities (pA/pF) evoked by 50 ms voltage ramps from −150 to +150 mV. (C) Average I/V relationships of CRACM3 currents extracted from representative cells shown in panel A at 120 s and 180 s in to the experiment (n=9). (D) Average normalized CRAC currents ($I/I_{120s}$) at −80 mV induced by $IP_3$ (20 µM) in stable STIM1-expressing HEK293 cells transiently overexpressing CRACM1 (indicated by "1"), CRACM2 (indicated by "2"), or CRACM3 (indicated by "3"). The bar indicates application of an external solution containing 10 mM $Ba^{2+}$ in the presence of $Na^+$. (E) Average normalized CRAC currents ($I/I_{120s}$) at −80 mV induced by $IP_3$ (20 µM) in stable STIM1-expressing HEK293 cells transiently overexpressing CRACM1 (indicated by "1") CRACM2 (indicated by "2"), or CRACM3 (indicated by "3"). The bar indicates application of an external solution containing 10 mM $Ba^{2+}$ with external $Na^+$ being replaced by $TEA^+$. (F) Average normalized CRAC currents ($I/I_{120s}$) at −80 mV induced by $IP_3$ (20 µM) in stable STIM1-expressing HEK293 cells transiently overexpressing CRACM1 (indicated by "1"), CRACM2 (indicated by "2"), or CRACM3

The selectivity profiles of all three proteins with respect to $Ca^{2+}$, $Ba^{2+}$, and $Na^+$ permeation were investigated (FIG. 4). When recording CRAC currents carried by the three homologs in the presence of 10 mM extracellular $Ca^{2+}$, all three homologs generated large inward currents at −80 mV (FIG. 4A) and exhibited similar inwardly rectifying I/V relationships (FIG. 4, B and C). When removing extracellular $Ca^{2+}$, inward currents were suppressed to the same degree in the three channel species (FIG. 4, A-C), demonstrating that they share similarly high $Ca^{2+}$ selectivity and discriminate against $Na^+$ ions as long as $Mg^{2+}$ ions (2 mM) are present.

The selectivity of the CRACM homologs for $Ba^{2+}$ ions was also investigated. FIG. 4D illustrates that equimolar substitution greatly reduces inward currents in CRACM1, suggesting that this protein can discriminate $Ca^{2+}$ ions against $Ba^{2+}$. In cells overexpressing CRACM2 or CRACM3, there remains significantly more inward current when $Ba^{2+}$ is used as charge carrier, which at first glance would indicate higher $Ba^{2+}$ permeation. However, since $Na^+$ ions remain present in the extracellular solution, there is also the possibility that $Na^+$ might contribute to inward current when $Ba^{2+}$ is present. When performing the same experiments as in FIG. 4D, but additionally replaced $Na^+$ by TEA, the inward currents through all three homologs are now essentially abolished (FIG. 4E), indicating that $Na^+$ ions rather than $Ba^{2+}$ may be carrying the additional current seen in FIG. 4D. To further assess the selectivity of CRACM channels, possible differences in $Na^+$ permeation were assessed in the complete absence of all divalent cations and additionally adding 10 mM EDTA to chelate any residual divalent cations. Under these conditions, CRAC channels become permeable to $Na^+$, typically generating a twofold increase in inward current in HEK293 cells overexpressing CRACM1 (FIG. 4F). The same experimental protocol produces slightly larger CRACM2 currents and CRACM3 generates a significantly larger monovalent current, again suggesting that the three CRACM homologs exhibit slightly different selectivities for $Na^+$ ions.

Example V

Pharmacology of CRACM Homologs

2-APB has previously been found to affect CRACM1 channels by potentiating CRAC currents at low concentrations ($\leq 5$ μM) and inhibiting them at high concentrations ($\geq 10$ μM). CRACM1 is completely inhibited by 50 μM 2-APB (see FIG. 4G). However, CRACM2 appears to be significantly less sensitive to 2-APB-mediated inhibition in that the same concentration reduced the current only by about 50%. The most striking effect, however, was observed with CRACM3, which was not inhibited but instead greatly potentiated by 2-APB.

Example VI

Selectivity Changes in CRACM3 in Response to 2-APB

HEK293 cells overexpressing CRACM3 were patch-clamped with pipette solutions in which the $Ca^{2+}$ concentration was clamped to ~150 nM in order to prevent store depletion and additionally contained 50 μM 2-APB to assess whether 2-APB can activate the channel when administered intracellularly. Under these conditions, no store-operated or 2-APB induced current was elicited, however, when 50 μM 2-APB was applied from the outside, it readily activated CRAC currents carried by CRACM3 (FIG. 6A). This would suggest that the facilitatory effect of 2-APB is either mediated through an extracellular site on the protein or that 2-APB acts within the membrane, but cannot access its site of action from the intracellular space.

The current-voltage relationship of the 2-APB-evoked current (FIG. 6D) exhibited significant rectification at negative and positive membrane voltages with a reversal potential of +30 mV, indicating that the selectivity of the channel had changed. Normally, CRAC currents are highly $Ca^{2+}$-selective and poorly permeable to $K^+$ or $Cs^+$, resulting in positive reversal potentials. The outward currents observed when exposing cells to 2-APB, however, revealed a significant increase in monovalent $Cs^+$ permeation and a large shift in reversal potential. This was assessed more quantitatively in STIM1-expressing cells that were additionally transfected with CRACM3 and measured CRAC currents evoked by $IP_3$ with intracellular solutions containing either $Cs^+$ or $K^+$ as main monovalent cation species. Under these conditions, CRAC currents due to $IP_3$-induced store depletion prior to 2-APB application were observed and their average reversal potential was +100 mV (n=4). 2-APB application produced large outward currents in both $Cs^+$- and $K^+$-based solutions and shifted the reversal potential to +31 mV for $Cs^+$ (n=4) and 29 mV for $K^+$. The average 2-APB-mediated current in these cells was approximately twice as large compared to CRACM3 currents without STIM1 overexpression.

Although 2-APB shifted the reversal potential of CRAC currents, it remained at positive potentials, suggesting that the channels retained some $Ca^{2+}$ permeability, consistent with the $Ca^{2+}$ entry observed in fura-2 measurements in intact cells. The monovalent versus divalent cation permeation was investigated in ion substitution experiments, where either $Ca^{2+}$ was removed from the extracellular solution or $Na^+$ was replaced by TEA. As illustrated in FIG. 6C, application of 2-APB in $Ca^{2+}$-free extracellular solution reduced the average inward current by 53% compared to $Ca^{2+}$-containing solutions, but nearly tripled the outward current. This was accompanied by a shift in reversal potential from +94 mV to +10 mV. This would suggest that $Ca^{2+}$ is responsible for a significant portion of the inward current and that it also impedes the outward movement of monovalent cations. At the same time, it is apparent that in the presence of 2-APB, CRAC channels are significantly more permeable to $Na^+$ ions, since normally, $Ca^{2+}$-free solutions completely suppress any inward currents through CRAC channels.

Conversely, removing $Na^+$ from the extracellular solution by replacing it with $TEA^+$ had no significant effect on inward or outward currents induced by 50 μM 2-APB. When considering the ionic concentrations and valences of these ions, CRAC channels retain preferential permeation of $Ca^{2+}$ over $Na^+$. Goldman-Hodgkin-Katz analysis of the reversal potentials in FIG. 6G yielded permeability ratios of $P_{Na}/P_{Cs}=1.5$ under $Ca^{2+}$-free conditions (blue I/V, $E_{rev}=+10$ mV) and $P_{Cs}/P_{Cs}=50$ (red I/V, +30 mV), which indicates a value of $P_{Ca}/P_{Na}=33$. It is clear that 2-APB causes a dramatic reduction in CRAC channel selectivity, as normally, CRAC channels feature $P_{Ca}/P_{Na}$ in excess of 100-fold.

Example VII

Effect of 2-APB on CRACM1 Pore Mutants

The above results demonstrate that 2-APB alters the selectivity of CRAC channels and it is conceivable that the mechanism by which 2-APB gates CRACM3 channels is linked to a widening of the selectivity filter, so that ions can permeate without the requirement of store depletion or STIM1 interaction. The degree of pore widening could determine the efficacy of 2-APB in gating the CRAC channel subtypes, with CRACM3 being the most susceptible, CRACM1 being just barely activatable, whereas CRACM2's pore being insufficiently widened by 2-APB to allow passage of ions without STIM1. Previous work has identified glutamate residues E106 in transmembrane domain TM1 and E190 in TM3 as critical determinants of selectivity of the CRACM1 pore.

Pore mutants with altered pore architecture and their response to 2-APB were investigated. Two CRACM1 mutants (E106D and E190A) were selected to test for 2-APB susceptibility. The E106D mutant of CRACM1 converts the normally inwardly rectifying channel into outwardly rectifying and shifts its reversal potential to +16 mV but has no constitutive channel activity and requires additional STIM1 overexpression and store depletion to produce large CRAC currents, suggesting that a simple alteration of pore selectivity does not result in store-independent gating.

HEK293 expressing the E106D mutant of CRACM1 alone had no constitutive CRAC currents and subsequent challenge with 50 µM 2-APB produced a complex response that typically produced a rapid increase in inward current, followed by complete block, and a slow reactivation after 2-APB application was suspended (FIG. 7A). After stopping 2-APB application, 2-APB molecules diffuse away and the local concentration decreases so that the CRAC channels can reactivate. The magnitude of the reactivated currents surpasses that of currents normally seen in cells that express CRACM1 channels alone in the absence of additional STIM1 overexpression, indicating that they result from store- and STIM1-independent gating of CRACM1. The current-voltage relationship of the reactivated current is essentially linear with a reversal potential of 0 mV (FIG. 7B), suggesting that 2-APB further shifts the reversal potential of the E106D mutant from +16 mV to the left.

The effect of 2-APB on the E190A mutant when expressed alone, without STIM1, in wild-type HEK293 cells was also analyzed. In these experiments, $IP_3$ was omitted from the pipette solution and buffered $[Ca^{2+}]_i$ to ~150 nM to avoid store depletion. This completely suppressed the development of any currents following establishment of the whole-cell configuration (FIG. 7E). Application of 50 µM 2-APB, however, produced a large, transient increase in both inward and outward current, whose I/V relationship (FIG. 7F) was similar to that observed in FIG. 7D where 2-APB facilitated store-operated E190A channels co-expressed with STIM1. Taken together, these data suggest that wild-type CRACM1 channels are largely resistant to store- and STIM1-independent gating by 2-APB, but modifications of residues E106 and E190, while not sufficient to gate the channel in a constitutive manner, enable 2-APB to further modify the pore architecture of CRACM1 so that the channels open in a store- and STIM1-independent manner. The results also suggest that this gating mode is favored at low 2-APB concentrations that build up at the start of 2-APB application and as the concentration in the membrane increases may transition into a state that no longer allows ion transport. Thus, 2-APB can both facilitate and inhibit CRAC channel function directly without requiring STIM1 overexpression.

---

SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: ribosome binding site

<400> SEQUENCE: 1

Ala Cys Cys Gly Cys Cys Ala Cys Cys
1               5

---

The E190 residue of CRACM1, which is also important for CRAC channel selectivity, was also assessed. When this glutamate residue is mutated to glutamine (E190Q), it shifts the reversal potential of the current to +50 mV and the I/V curve exhibits both inward and outward rectification. The E190Q mutant was marginally effective in restoring SOCE in T cells with defective $Ca^{2+}$ influx derived from SCID patients, whereas E190A and E190D mutants fully restored $Ca^{2+}$ influx. FIG. 7C illustrates that when the E190A mutant is co-expressed with STIM1, it responds similarly as wild-type CRACM1 when $IP_3$ is perfused into cells. It activated rapidly following store depletion and its I/V relationship was similar to that of wild-type channels in that it exhibited strong inward rectification (FIG. 7D), although its reversal potential was shifted to +55 mV, similar to the E190Q mutant. Thus, this mutant appears to have an intermediate phenotype in that it also changes the selectivity of CRACM1, but outward transport of $Cs^+$ appears to be significantly less than seen with the E190Q mutant. When exposing cells to 50 µM 2-APB after CRAC currents had fully activated, the compound evoked a large facilitation followed by rapid inhibition (FIG. 7C), qualitatively similar to wild-type CRACM1, but with a more pronounced facilitation. The facilitated current was characterized by a larger outward current and a leftward shift in reversal potential to +33 mV (FIG. 7D), again demonstrating that 2-APB lowers the selectivity of CRAC channels.

What is claimed is:

1. An assay to determine if CRACM3 contributes to the Icrac activity of a cell expressing CRACM3, the assay comprising measuring Icrac activity of said cell at a concentration of ≥50 µM 2-aminoethoxydiphenyl borate (2-APB) and comparing that Icrac activity of a cell in the absence of 2-APB, wherein an increase in said Icrac activity in the presence of said 2-APB as compared to said Icrac activity in the absence of 2-APB indicates that CRACM3 contributes to said Icrac activity of said cell.

2. The assay of claim 1 further comprising measuring Icrac activity of said cell at a concentration ≤5 µM 2-APB and at a concentration ≥10 µM 2-APB, wherein potentiation at ≤5 µM 2-APB and inhibition of Icrac current in the presence of ≥10 µM 2-APB indicates a contribution of CRACM1 to said Icrac activity.

3. The assay of claim 1 or 2 wherein said Icrac activity is selected from the group consisting of Icrac inactivation kinetics, Icrac activation kinetics and Icrac calcium entry of said cell.

4. The assay claim 1 or 2 wherein said cell transiently over expresses said CRACM3.

5. The assay of claim 4 wherein said cell expresses STIM1.

* * * * *